(12) United States Patent
Beard et al.

(10) Patent No.: US 11,690,742 B2
(45) Date of Patent: Jul. 4, 2023

(54) DELIVERY AND DEPLOYMENT SYSTEMS FOR BIFURCATED STENT GRAFTS

(71) Applicant: W. L. Gore & Associates, Inc., Newark, DE (US)

(72) Inventors: Matthew S. Beard, Phoenix, AZ (US); Martin J. Sector, Gilbert, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 1287 days.

(21) Appl. No.: 15/983,186

(22) Filed: May 18, 2018

(65) Prior Publication Data

US 2018/0263800 A1    Sep. 20, 2018

Related U.S. Application Data

(63) Continuation of application No. 14/675,368, filed on Mar. 31, 2015, now Pat. No. 9,974,675.
(Continued)

(51) Int. Cl.
*A61F 2/954* (2013.01)
*A61F 2/07* (2013.01)
*A61F 2/06* (2013.01)

(52) U.S. Cl.
CPC .............. *A61F 2/954* (2013.01); *A61F 2/07* (2013.01); *A61F 2002/065* (2013.01)

(58) Field of Classification Search
CPC ...... A61F 2/07; A61F 2/954; A61F 2002/065; A61F 2/966; A61F 2002/9586;
(Continued)

(56) References Cited

U.S. PATENT DOCUMENTS

| 5,609,627 A | * | 3/1997 | Goicoechea | ............... A61F 2/82 |
| | | | | 128/898 |
| 5,792,144 A | * | 8/1998 | Fischell | ................... A61F 2/958 |
| | | | | 606/108 |

(Continued)

FOREIGN PATENT DOCUMENTS

| CN | 101330882 A | * | 12/2008 | ............ A61B 17/064 |
| CN | 102188296 A | * | 9/2011 | ....... A61B 17/00234 |

(Continued)

OTHER PUBLICATIONS

English Translation CN 101330882 (Year: 2008).*
(Continued)

*Primary Examiner* — Ashley L Fishback
*Assistant Examiner* — Erin L Colello

(57) ABSTRACT

A system for endoluminal delivery of a medical device, wherein the medical device includes a bifurcated stent graft having a trunk, a first leg and a second leg shorter than the first leg. The system includes a sheath having a tubular wall having a cylindrical inner surface defining a lumen for receiving the stent graft therein to constrain the stent graft toward a delivery configuration suitable for endoluminal delivery, and a generally cylindrical core member extending through the lumen. The core member has a first annular surface for engaging an end of the first leg. The core has a second annular surface for engaging an end of the second leg while at least the end of the second leg remains constrained by the sheath.

21 Claims, 4 Drawing Sheets

Related U.S. Application Data

(60) Provisional application No. 61/975,217, filed on Apr. 4, 2014.

(58) Field of Classification Search
CPC ........ A61F 2002/067; A61F 2002/9534; A61F 2002/9528; A61F 2/9522; A61F 2/95
See application file for complete search history.

(56) References Cited

U.S. PATENT DOCUMENTS

| | | | |
|---|---|---|---|
| 5,860,998 A * | 1/1999 | Robinson | A61F 2/07 606/108 |
| 5,928,248 A * | 7/1999 | Acker | A61B 5/06 128/898 |
| 6,120,522 A * | 9/2000 | Vrba | A61F 2/95 606/190 |
| 6,203,550 B1 | 3/2001 | Olson | |
| 6,241,758 B1 * | 6/2001 | Cox | A61F 2/95 606/108 |
| 6,352,561 B1 | 3/2002 | Leopold et al. | |
| 6,551,350 B1 | 4/2003 | Thornton et al. | |
| 6,689,156 B1 * | 2/2004 | Davidson | A61B 8/12 606/108 |
| 6,692,494 B1 * | 2/2004 | Cooper | A61B 8/12 128/898 |
| 6,733,521 B2 | 5/2004 | Chobotov et al. | |
| 6,911,039 B2 | 6/2005 | Shiu | |
| 6,951,572 B1 * | 10/2005 | Douglas | A61F 2/07 623/1.13 |
| 6,974,471 B2 | 12/2005 | Van Schie | |
| 7,081,132 B2 | 7/2006 | Cook | |
| 7,147,661 B2 | 12/2006 | Chobotov | |
| 7,435,253 B1 * | 10/2008 | Hartley | A61F 2/954 623/1.12 |
| 7,550,002 B2 | 6/2009 | Goto | |
| 7,655,034 B2 | 2/2010 | Mitchell et al. | |
| 7,837,724 B2 | 11/2010 | Keeble | |
| 7,938,851 B2 | 5/2011 | Olson | |
| 7,976,575 B2 | 7/2011 | Hartley | |
| 8,109,983 B2 * | 2/2012 | Gunderson | A61F 2/966 623/1.11 |
| 8,167,927 B2 | 5/2012 | Chobotov | |
| 8,211,167 B2 * | 7/2012 | Vardi | A61F 2/958 623/1.35 |
| 8,241,346 B2 | 8/2012 | Chobotov | |
| 8,257,431 B2 | 9/2012 | Henderson | |
| 8,262,671 B2 | 9/2012 | Osypka | |
| 8,328,861 B2 | 12/2012 | Martin | |
| 8,361,135 B2 | 1/2013 | Dittman | |
| 8,480,725 B2 | 7/2013 | Rasmussen | |
| 8,968,384 B2 | 3/2015 | Pearson | |
| 9,060,895 B2 | 6/2015 | Hartley | |
| 9,132,025 B2 | 9/2015 | Aristizabal | |
| 9,254,204 B2 | 2/2016 | Roeder | |
| 9,308,349 B2 | 4/2016 | Rezac | |
| 9,498,361 B2 | 11/2016 | Roeder | |
| 9,585,743 B2 | 3/2017 | Cartledge | |
| 9,585,774 B2 | 3/2017 | Aristizabal | |
| 9,681,968 B2 | 6/2017 | Goetz | |
| 9,700,701 B2 | 7/2017 | Benjamin | |
| 9,782,284 B2 | 10/2017 | Hartley | |
| 9,937,070 B2 | 4/2018 | Skelton | |
| 9,974,675 B2 | 5/2018 | Beard et al. | |
| 2001/0037141 A1 * | 11/2001 | Yee | A61M 25/00 623/1.11 |
| 2002/0198587 A1 * | 12/2002 | Greenberg | A61F 2/07 623/1.13 |
| 2003/0074047 A1 * | 4/2003 | Richter | A61F 2/07 623/1.11 |
| 2004/0230286 A1 | 11/2004 | Moore et al. | |
| 2004/0267348 A1 * | 12/2004 | Gunderson | A61F 2/91 623/1.12 |
| 2005/0049609 A1 * | 3/2005 | Gunderson | A61F 2/95 606/108 |
| 2005/0050015 A1 | 3/2005 | Becker | |
| 2006/0229697 A1 * | 10/2006 | Gerdts | A61F 2/966 623/1.11 |
| 2007/0050015 A1 * | 3/2007 | O'Brien | A61F 2/966 623/1.35 |
| 2008/0132906 A1 | 6/2008 | Rasmussen | |
| 2009/0024072 A1 * | 1/2009 | Criado | A61B 17/12045 604/9 |
| 2009/0132026 A1 * | 5/2009 | Martin | A61F 2/954 623/1.23 |
| 2009/0259296 A1 | 10/2009 | Mciff et al. | |
| 2009/0259298 A1 * | 10/2009 | Mayberry | A61F 2/97 623/1.35 |
| 2010/0049293 A1 | 2/2010 | Zukowski | |
| 2011/0251664 A1 | 10/2011 | Acevedo | |
| 2013/0053945 A1 | 2/2013 | Greenberg et al. | |
| 2014/0018913 A1 | 1/2014 | Cartledge | |
| 2014/0046317 A1 * | 2/2014 | Truckai | A61B 90/04 606/33 |
| 2014/0172067 A1 * | 6/2014 | Brown | A61B 90/39 623/1.12 |
| 2017/0172724 A1 | 6/2017 | Cartledge | |
| 2017/0281382 A1 | 10/2017 | Lostetter | |

FOREIGN PATENT DOCUMENTS

| | | | | |
|---|---|---|---|---|
| CN | 103037817 A | | 4/2013 | |
| EP | 0684022 A2 * | | 11/1995 | |
| EP | 1474074 B1 | | 4/2004 | |
| EP | 1441668 B1 | | 1/2008 | |
| EP | 1915113 B1 | | 3/2010 | |
| EP | 1358903 B1 | | 2/2011 | |
| EP | 2749251 B1 | | 7/2016 | |
| EP | 2956198 B1 | | 11/2017 | |
| FR | 2748197 A1 * | | 11/1997 | A61F 2/95 |
| WO | WO-9853761 A1 * | | 12/1998 | A61F 2/07 |
| WO | WO-1998053761 | | 12/1998 | |
| WO | WO-2007025101 A2 | | 3/2007 | |
| WO | WO-2008066917 A1 | | 6/2008 | |

OTHER PUBLICATIONS

English Translation CN 102188296 (Year: 2011).*
International Preliminary Reporton Patentability received for PCT Patent Application No. PCT/US2015/023874, dated Oct. 13, 2016, 7 pages.
International Search Report and Written Opinion for PCT/US2015/023874 dated Jul. 8, 20151 corresponding to U.S. Appl. No. 14/675,368, 5 pages.

* cited by examiner

DELIVERY AND DEPLOYMENT SYSTEMS FOR BIFURCATED STENT GRAFTS

CROSS-REFERENCE TO RELATED APPLICATION

This application is a continuation of U.S. patent application Ser. No. 14/675,368, filed Mar. 31, 2015, now U.S. Pat. No. 9,974,675, issued May 22, 2018, which claims the benefit of U.S. Provisional Application 61/975,217, filed Apr. 4, 2014, both of which are incorporated herein by reference in their entireties for all purposes.

BACKGROUND

The present disclosure relates to medical device deployment systems. More particularly, the present disclosure relates to deployment system for bifurcated stent grafts.

DISCUSSION OF THE RELATED ART

There is a need for advanced devices, tools, systems and methods used for the endoluminal treatment of aortic diseases. In particular, there remains a need for deployment systems that can accommodate increasingly complex modes of deployment of a device, such as steering, reconstraining, multiple stage deployment, multiple device deployment, while promoting ease of use to the clinician. There also remains a need for increasingly reduced profile delivery mechanisms.

BRIEF DESCRIPTION OF THE DRAWINGS

The accompanying drawings are included to provide a further understanding of the present disclosure and are incorporated in and constitute a part of this specification, illustrate embodiments of the present disclosure, and together with the description serve to explain the principles of the present disclosure.

DETAILED DESCRIPTION

Figure 1:
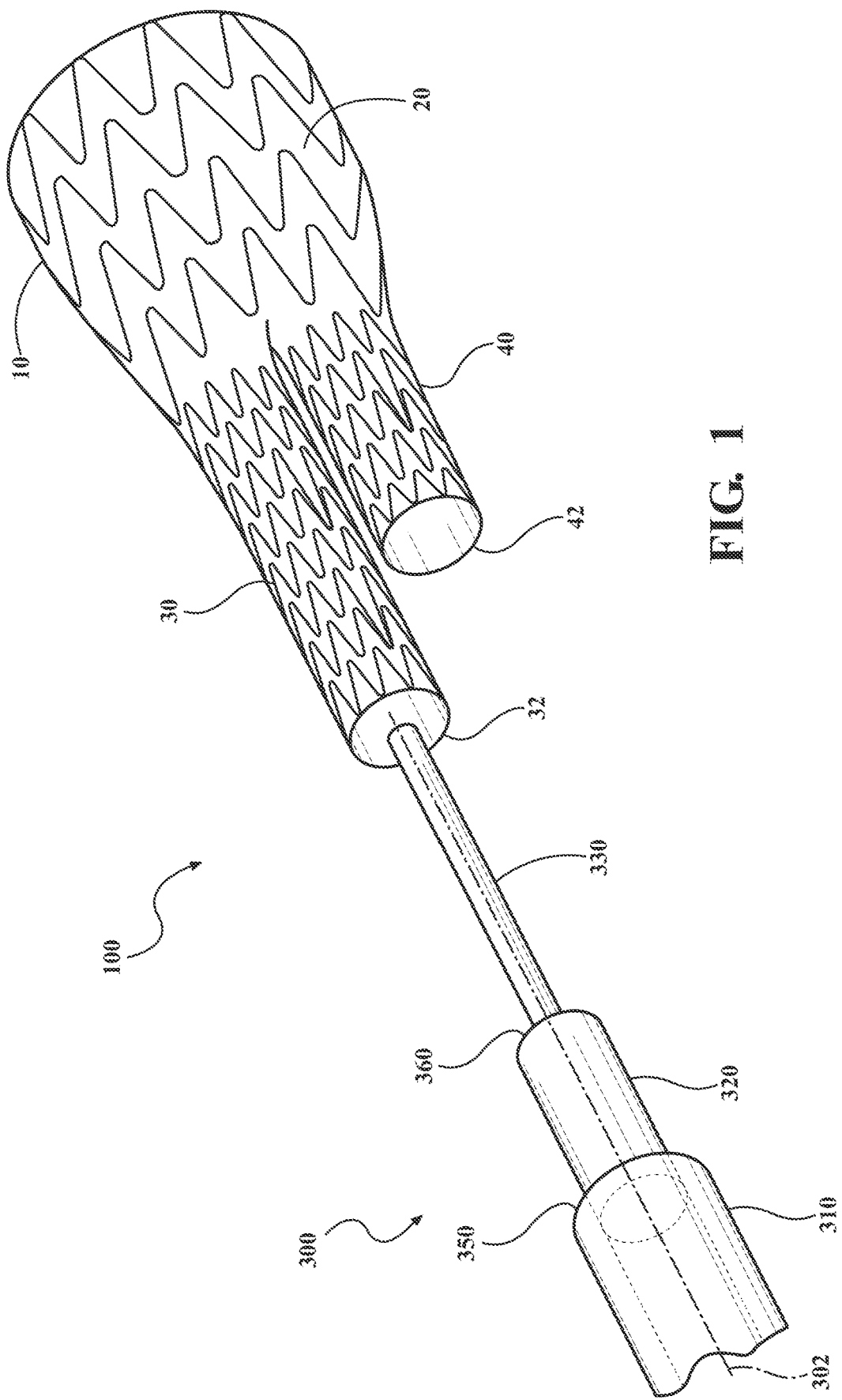
FIGS. 1-3 illustrate a bifurcated stent graft and a portion of a deployment system in accordance with various embodiments.

In various embodiments, a system for endoluminal delivery of a medical device includes a bifurcated stent graft comprising a trunk, a first leg and a second leg, wherein the first leg is longer than the second leg; a sheath having a tubular wall having a cylindrical inner surface defining a lumen for receiving the stent graft therein to constrain the stent graft toward a delivery configuration suitable for endoluminal delivery; and a generally cylindrical core member extending through the lumen, the core member having a first section having a first diameter, a second section having a second diameter smaller than the first diameter, and a third section having a third diameter smaller than the second diameter, the core having an annular first end surface between the first and second sections, and an annular second end surface between the second and third sections, wherein the first and second ends surfaces of the core member engage respective axially spaced apart portions of the stent graft during axial displacement of the sheath with respect to the core member.

Referring to FIGS. 1-8, for example, a delivery system for delivery of a bifurcated stent graft 10 is generally indicated at 100. As shown, the stent graft 10 includes a trunk 20, a first leg 30 and a second leg 40, wherein the first leg 30 is longer than the second leg 40. The delivery system 100 includes a sheath 200 having a tubular wall 210. The tubular wall includes an outer surface 212 and an opposite inner surface 214 defining a lumen 216. The lumen 216 is configured to receive the stent graft 10 therein to constrain and maintain the stent graft 10 in a delivery configuration suitable for endoluminal delivery to a vascular treatment site.

The delivery system 100 includes a core member 300. The core member 300 has a longitudinal axis 302 and through the lumen 216 of the sheath 200. The core member 300 includes a first section 310 having a first diameter. The core member 300 includes a second section 320 having a second diameter smaller than the first diameter. The core member 300 includes a third section 330 having a third diameter smaller than the second diameter.

The core member 300 includes an annular first end surface 350 between the first 310 and second 320 sections. The first end surface 350 can be substantially normal to the longitudinal axis 302 of the core member 300. Similarly, the core member 300 includes an annular second end surface 360 between the second 320 and third 330 sections. The second end surface 360 can be substantially normal to the longitudinal axis 302 of the core member 300.

Figure 2:
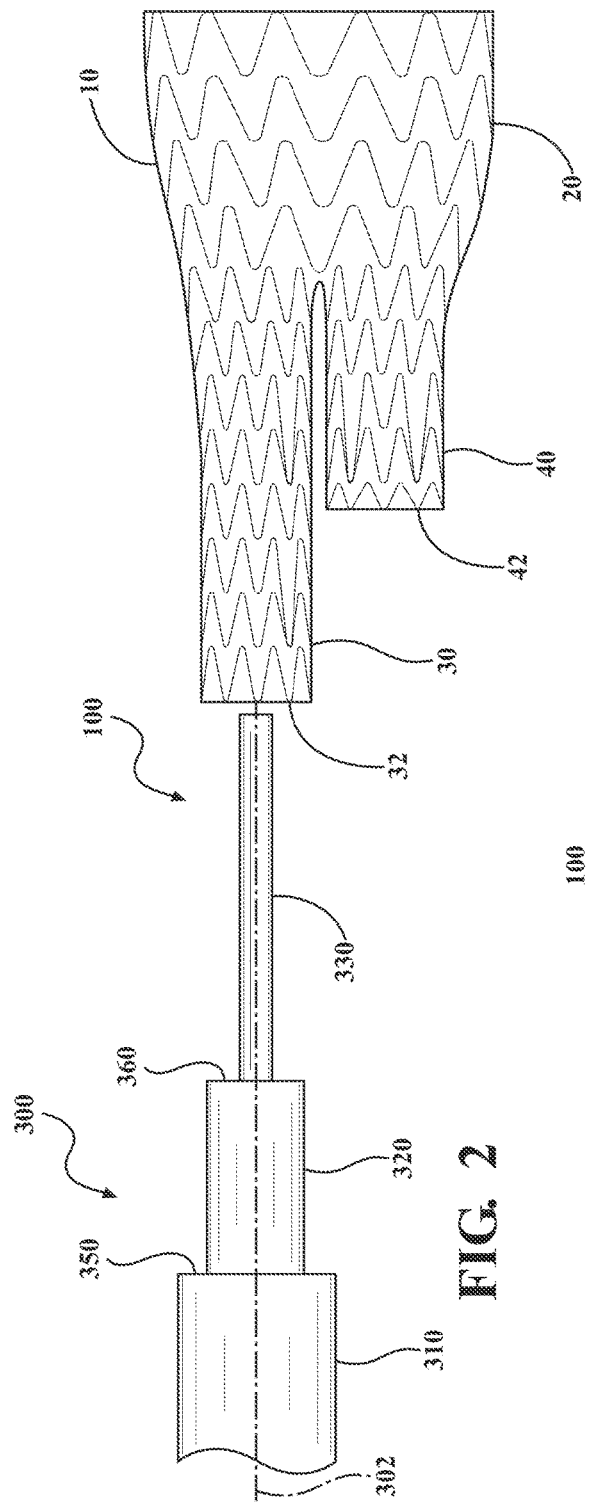
Figure 3:
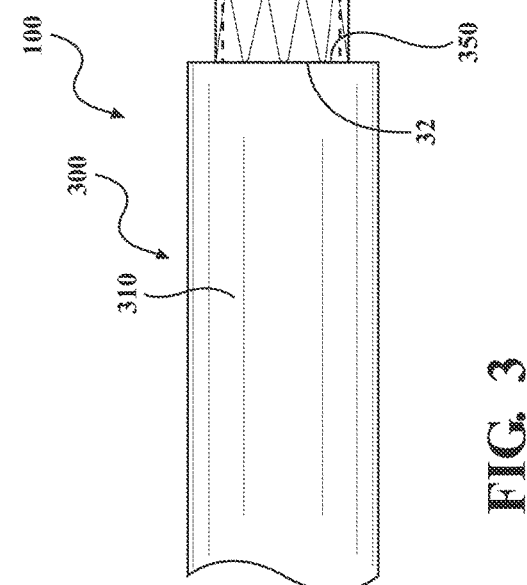
Figure 4:
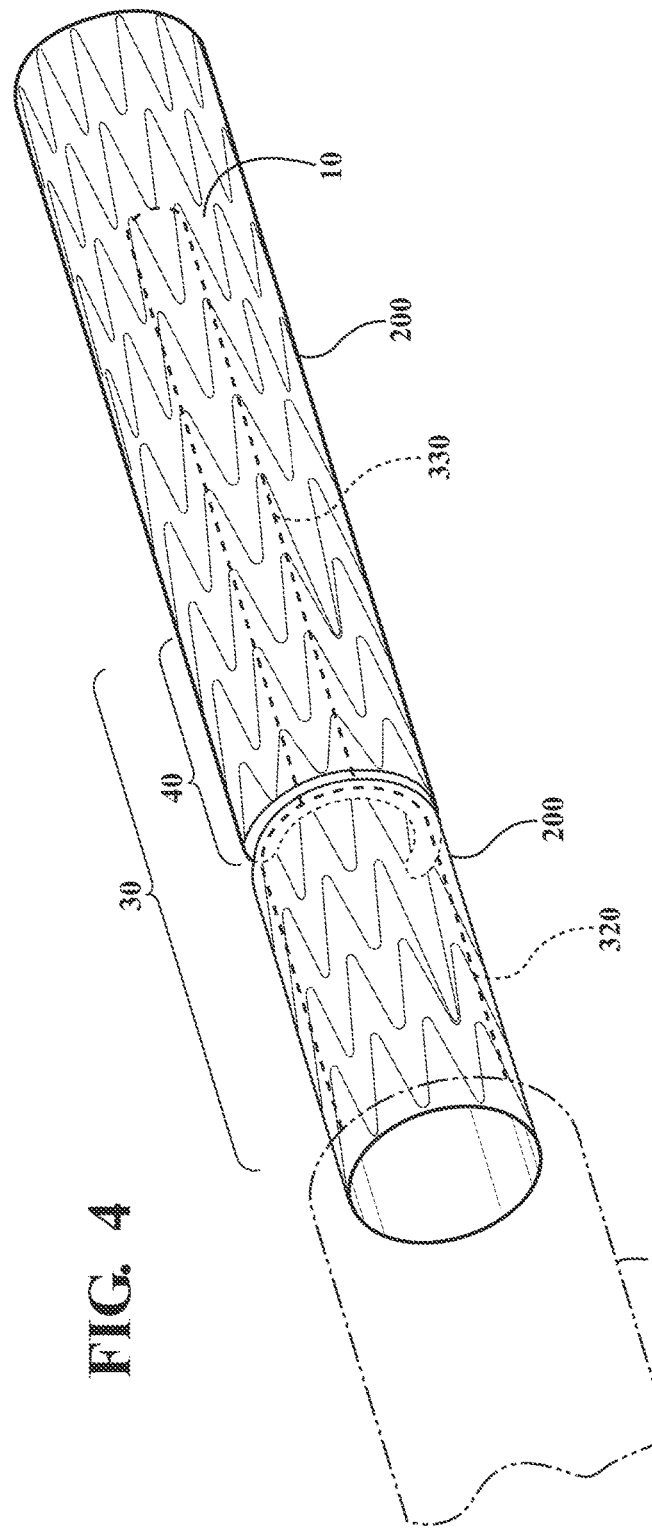
FIGS. 4-5 illustrate a bifurcated stent graft retained in a delivery configuration by a deployment system in accordance with various embodiments.
Figure 5:
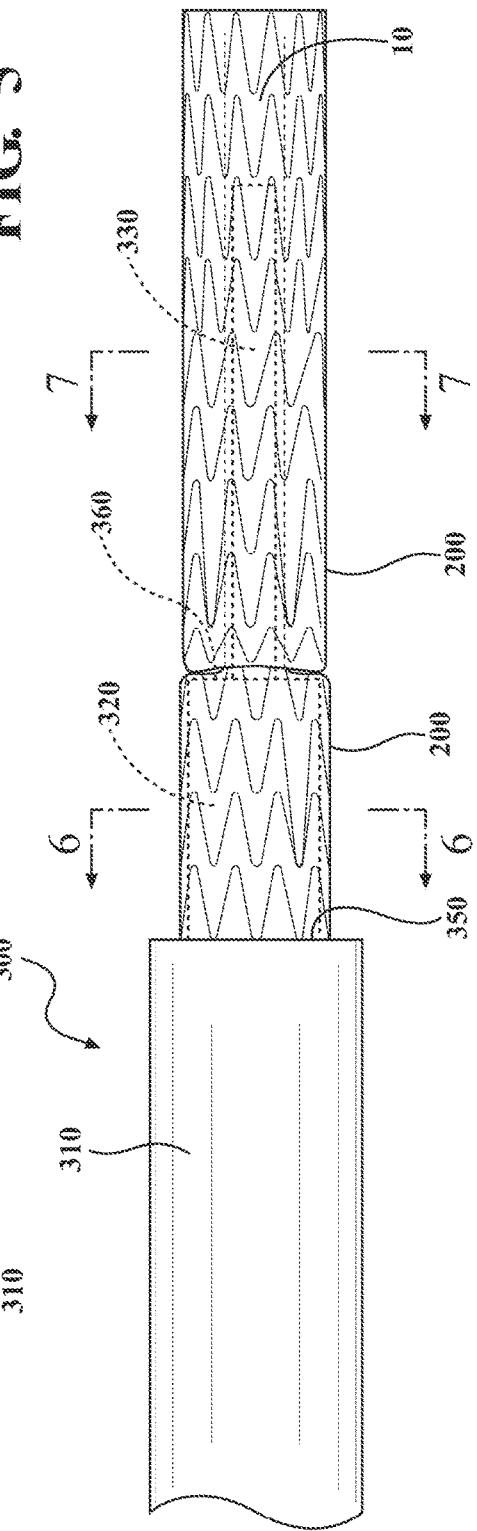
Figure 7:
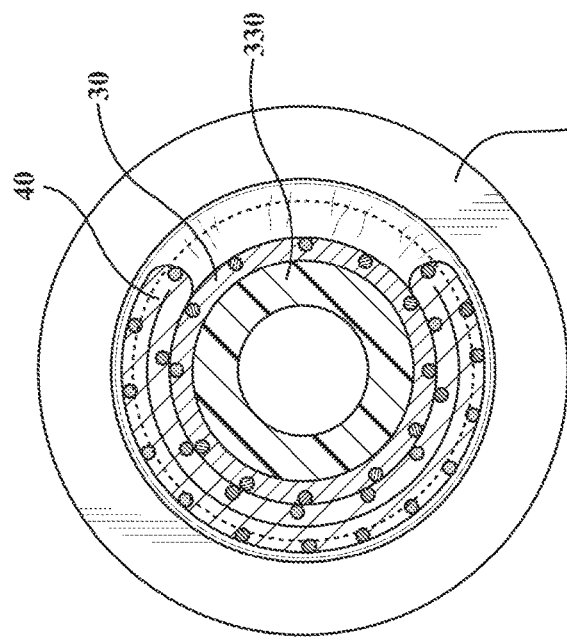
FIGS. 6-7 are cross sectional views of the bifurcated stent graft and deployment system as taken along planes indicated at 6-6 and 7-7 in FIG. 5, respectively.
Figure 6:
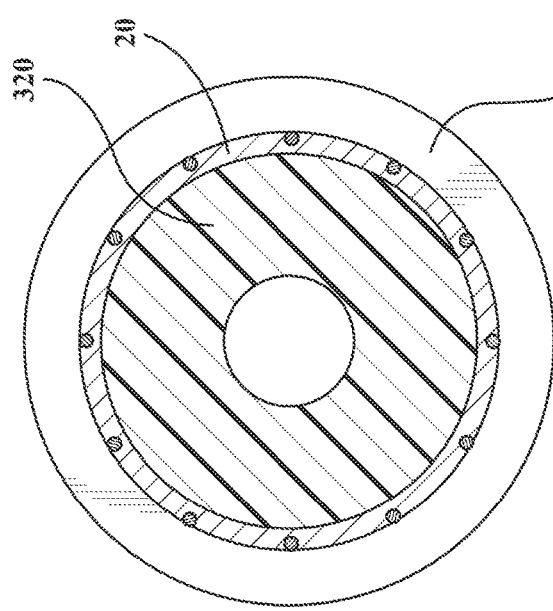
Figure 8:
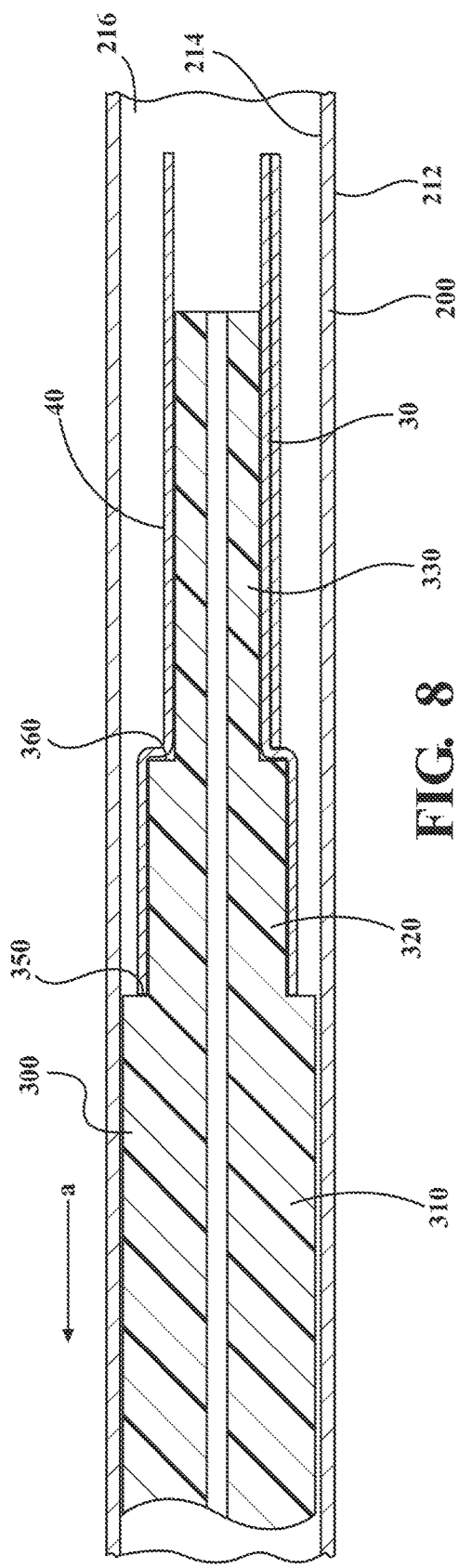
FIG. 8 is a longitudinal cross sectional view of the bifurcated stent graft and deployment system in FIG. 5.

During assembly, the core member 300 can be inserted through the first leg 30 of the stent graft 10, as shown in FIG. 1, until a terminal end 32 of the first leg 30 abuts the first end surface 350, as shown in FIGS. 2 and 3. A terminal end 42 of the second leg 40 of the stent graft 10 is generally aligned axially with the second end surface 360, as indicated at plane "P" in FIG. 3.

With the stent graft 10 mounted in the configuration shown in FIG. 3, the stent graft 10 is then compacted generally radially onto the core member 300 and retained in the delivery configuration by the sheath 200, as shown in FIGS. 4-8. As best shown in the cross sectional view of FIG. 7 (taken along the plane indicated at 7-7 in FIG. 5), the second leg 40 is compacted along a portion of a circumference of the third section 330, while the first leg 30 is compacted and generally co-axially aligned with the third section 330.

By this arrangement, the second leg 40 adds column strength to the stent graft 10 along the core member 300 to help prevent axial crumpling of the stent graft 10 during axial displacement of the sheath 200 relative to the core. Thus, during deployment of the stent graft 10, the sheath 200 is displaced axially along a direction, generally indicated by arrow "a" in FIG. 8, relative to the core member 300. Abutment between the terminal ends 32 and 42 of the first 30 and second 40 legs, respectively, and the first 350 and second 360 end surfaces prevents axial displacement of the stent graft 10 due to friction between the stent graft 10 and the sheath 10 as the sheath 10 is displaced. The enhanced column strength of the compacted stent graft along the third section 330 of the core member 300 also helps to resist axial crumpling the stent graft also due to friction between the stent graft 10 and the sheath 10 as the sheath 10 is displaced relative to the core member 300.

Axial displacement of the sheath 10 relative to the core member 300 allows outward expansion of the stent graft 10 from the delivery configuration. Optionally, secondary sheaths or constraining sleeves can be utilized to limit expansion of the stent graft to an intermediate configuration larger than the delivery configuration and smaller than a fully deployed configuration engaged with vessel walls. Further details of such constraining sleeves can be found, for example, in U.S. Pat. No. 6,352,561 issued to Leopold, et al., U.S. Pat. No. 6,551,350 issued to Thornton, et al., as well as co-pending U.S. Patent Application Publication US 2010/0049293 A1 (Zukowski et al.), the content of which is incorporated herein by reference in its entirety.

Upon full deployment of the stent graft 10, the core member 300 and sheath 200 can be removed from the treatment site and body of the patient.

It will be apparent to those skilled in the art that various modifications and variations can be made in the present present disclosure without departing from the spirit or scope of the present disclosure. Thus, it is intended that the present present disclosure cover the modifications and variations of this present disclosure provided they come within the scope of the appended claims and their equivalents.

What is claimed is:

1. An endoluminal delivery system comprising:
   a bifurcated stent graft having a trunk, a first leg and a second leg shorter than the first leg;
   a sheath having a tubular wall having an inner surface defining a lumen for receiving the stent graft therein to constrain the stent graft toward a delivery configuration suitable for endoluminal delivery; and
   a core member having a first surface and a second annular surface, the core member extending into a lumen of the first leg such that the first surface abuts an end of the first leg, the second surface is-positioned within the lumen of the first leg such that the first leg is disposed between the second surface and the second leg, and a terminal end of the second leg is generally aligned in an axial direction with and abuts the second annular surface, where the second surface is obstructing the end of the second leg while the end of the second leg remains constrained by the sheath.

2. The system of claim 1, wherein the core member is generally cylindrical and includes a first section having a first diameter and a second section having a second diameter, the first diameter being larger than the second diameter, and wherein the first surface is a first annular surface and defines a transition between an outer surface of the first section and an outer surface of the second section.

3. The system of claim 2, wherein the first annular surface is normal relative to a longitudinal axis of the core member.

4. The system of claim 2, wherein the core member includes a third section having a third diameter, the second diameter being larger than the third diameter, and wherein the second surface defines a transition between the outer surface of the second section and an outer surface of the third section.

5. The system of claim 4, wherein a difference between the second diameter and the third diameter is at least twice the sum of a thickness of the first leg and twice a thickness of the second leg.

6. The system of claim 4, wherein the second annular surface is normal relative to a longitudinal axis of the core member.

7. The system of claim 4, wherein the first, second, and third sections of the core member are coaxial.

8. The system of claim 1, wherein the first surface and the second surface are parallel.

9. The system of claim 1, wherein the second leg is configured to add column strength along the core member to resist axial crumpling of the stent graft while the second surface obstructs the end of the second leg and the end of the second leg remains constrained by the sheath.

10. A medical device delivery system, said system comprising:
    a bifurcated stent graft having a proximal end and a distal end opposite the proximal end, the stent graft having a trunk extending between the proximal end and a bifurcation, the stent graft having first and second legs extending distally from the bifurcation, the first leg having an end defining the distal end of the stent graft, the second leg having an end terminating at a location between the bifurcation and the distal end of the stent graft;
    a sheath disposed about the stent graft for constraining the stent graft toward a delivery configuration suitable for endoluminal delivery; and
    a core member having a first surface for engaging the distal end of the stent graft, the core member having a second annular surface and extending into a lumen of the first leg, the second surface positioned within the lumen of the first leg such that the first leg is disposed between the second surface and the second leg, where a terminal end of the second leg is generally aligned in an axial direction with and abuts the second annular surface, and wherein the second annular surface is adapted to engage the end of the second leg during displacement of the sheath relative to the core member.

11. The system of claim 10, wherein the core member extends into the lumen of the first leg such that the first surface is positioned distal to the second surface.

12. The system of claim 10, wherein the second surface is adapted to engage the end of the second leg during displacement of the sheath relative to the core member while the end of the second leg is constrained by the sheath.

13. The system of claim 10, wherein the core member is generally cylindrical and includes a first section having a first diameter, a second section having a second diameter, and a third section having a third diameter, the second diameter being larger than the third diameter, wherein the first surface is a first annular surface that defines a transition between the first section and the second section, and wherein the second surface defines a transition between the second section and the third section.

14. The system of claim 13, wherein a difference between the second diameter and the third diameter is at least twice the sum of a thickness of the first leg and twice a thickness of the second leg.

15. The system of claim 13, wherein the first and second sections of the core member are coaxially aligned.

16. The system of claim 10, wherein the second surface is normal relative to a longitudinal axis of the core member.

17. An endoluminal delivery system comprising:
    a bifurcated stent graft having a trunk, a first leg and a second leg shorter than the first leg;
    a sheath having a tubular wall having an inner surface defining a lumen for receiving the stent graft therein to constrain the stent graft toward a delivery configuration suitable for endoluminal delivery; and
    a core member extending into a lumen of the first leg, the core member having a first annular surface and a second annular surface, the second annular surface being adapted to obstruct axial displacement of the bifurcated stent graft by obstructing an end of the second leg while the second annular surface is positioned within the lumen of the first leg such that the first leg is disposed between the second annular surface and the second leg, and a terminal end of the second leg is generally aligned in an axial direction with and abuts the second annular surface, while the first annular surface abuts an end of the first leg.

18. The system of claim 17, wherein the second annular surface is adapted to obstruct the end of the second leg while the end of the second leg is constrained by the sheath.

19. The system of claim 17, wherein the core member extends into the lumen of the first leg such that the second annular surface is positioned within the lumen of the first leg between the end of the second leg and the end of the first leg.

20. The system of claim 17, wherein the core member includes a first section having a first diameter, a second section having a second diameter, and a third section having a third diameter, the second diameter being larger than the third diameter, the first annular surface defining a transition between the first section and the second section, and the second annular surface defining a transition between the second section and the third section.

21. The system of claim 20, wherein a difference between the second diameter and the third diameter is at least twice the sum of a thickness of the first leg and twice a thickness of the second leg.

\* \* \* \* \*